United States Patent [19]

Pelrine

[11] Patent Number: 4,914,254

[45] Date of Patent: Apr. 3, 1990

[54] FIXED BED PROCESS FOR HIGH VISCOSITY INDEX LUBRICANT

[75] Inventor: Bruce P. Pelrine, Trenton, N.J.

[73] Assignee: Mobil Oil Corporation, New York, N.Y.

[21] Appl. No.: 282,769

[22] Filed: Dec. 12, 1988

[51] Int. Cl.⁴ .............................................. C07C 2/02
[52] U.S. Cl. ...................................... 585/530; 585/10
[58] Field of Search .................................. 585/10, 530

[56] References Cited

U.S. PATENT DOCUMENTS

| | | | |
|---|---|---|---|
| 2,825,721 | 3/1958 | Hoqam et al. | 585/530 |
| 4,827,064 | 5/1989 | Wu | 585/10 |
| 4,827,073 | 5/1989 | Wu | 585/530 |

Primary Examiner—Curtis R. Davis
Attorney, Agent, or Firm—Alexander J. McKillop; Charles J. Speciale; Malcolm D. Keen

[57] ABSTRACT

A process is disclosed to produce liquid oligomers from alpha-olefins feedstock, such as 1-decene, wherein said oligomers have branch ratios below 0.19 and have higher viscosity indices than oligomers with higher branch ratios. The olefins can be oligomerized over a supported and reduced metal oxide catalyst from Group VIB of the Periodic Table to give oligomers suitable for lubricant application. A preferred catalyst is lower valence state chromium on silica support. Surprisingly, it has been found that in the oligomerization of the alpha-olefins in a fixed bed reactor containing extruded catalyst the viscosity of the lubricant produced can be selectively controlled by carrying out the oligomerization at essentially constant oligomerization temperature while varying the olefin feedstock weight hourly space velocity (WHSV), based on catalyst, in correspondence with the preferred product viscosity.

11 Claims, 3 Drawing Sheets

FIXED BED PROCESS FOR HIGH VISCOSITY INDEX LUBRICANT

This invention relates to a process for the production of high viscosity index synthetic lubricant fluids. More particularly, the invention relates to a fixed bed oligomerization process for the production of synthetic hydrocarbon lubricants providing improved viscosity control.

BACKGROUND OF THE INVENTION

Catalytic oligomerization of olefins is a known technique for manufacturing hydrocarbon basestocks useful as lubricants. Efforts to improve upon the performance of natural mineral oil based lubricants by the synthesis of oligomeric hydrocarbon fluids have been the subject of important research and development in the petroleum industry for many years and have led to the relatively recent market introduction of a number of superior polyalpha-olefin (PAO) synthetic lubricants, primarily based on the oligomerization of alpha-olefins or 1-alkenes. In terms of lubricant property improvement, the thrust of the industrial research effort on synthetic lubricants has been toward fluids exhibiting useful viscosities over a wide range of temperature, i.e., improved viscosity index, while also showing lubricity, thermal and oxidative stability and pour point equal to or better than mineral oil. These new synthetic lubricants lower friction and hence increase mechanical efficiency across the full spectrum of mechanical loads from work gears to traction drives and do so over a wider range of operating conditions than mineral oil lubricants.

The chemical focus of the research effort in synthetic lubricants has been on the polymerization of 1-alkenes. Well known structure/property relationships for high polymers as contained in the various disciplines of polymer chemistry have pointed the way to 1-alkenes as a fruitful field of investigation for the synthesis of oligomers with the structure thought to be needed to confer improved lubricant properties thereon. Due largely to studies on the polymerization of propene and vinyl monomers, the mechanism of the polymerization of 1-alkene and the effect of that mechanism on polymer structure is reasonably well understood providing a strong resource for targeting on potentially useful oligomerization methods and oligomer structures. Building on that resource, in the prior art oligomers of 1-alkenes from $C_6$ to $C_{20}$ have been prepared with commercially useful synthetic lubricants from 1-decene oligomerization yielding a distinctly superior lubricant product via either cationic or Ziegler catalyzed polymerization.

One characteristic of the molecular structure of 1-alkene oligomers that has been found to correlate very well with improved lubricant properties in commercial synthetic lubricants is the ratio of methyl to methylene groups in the oligomer. The ratio is called the branch ratio and is calculated from infra red data as discussed in "Standard Hydrocarbons of High Molecular Weight", *Analytical Chemistry*, Vol. 25, no. 10, p. 1466 (1953). Viscosity index has been found to increase with lower branch ratio. Heretofore, oligomeric liquid lubricants exhibiting very low branch ratios have not been synthesized from 1-alkenes. For instance, oligomers prepared from 1-decene by either cationic polymerization or Ziegler catalyst polymerization have branch ratios of greater than 0.20. Shubkin, *Ind. Eng. —Chem. Prod. Res. Dev.* 1980, 19, 15–19, provides an explanation for the apparently limiting value for branch ratio based on a cationic polymerization reaction mechanism involving rearrangement to produce branching. Other explanations suggest isomerization of the olefinic group in the one position to produce an internal olefin as the cause for branching. Whether by rearrangement, isomerization or a yet to be elucidated mechanism it is clear that in the art of 1-alkene oligomerization to produce synthetic lubricants as practiced to-date, excessive branching occurs and constrains the limits of achievable lubricant properties, particularly with respect to viscosity index. Obviously, increased branching increases the number of isomers in the oligomer mixture, orienting the composition away from the structure which would be preferred from a consideration of the theoretical concepts discussed above.

In the HVI-PAO process as practiced heretofore, while a wide range of lubricant viscosities can be prepared by direct synthesis, viscosity has been found to vary only by varying reaction temperature. Lower viscosity product is prepared at high reaction temperatures which leads to rapid catalyst aging and more frequent catalyst regeneration.

Accordingly, it is an object of the present invention to provide an improved fixed bed process for the production of HVI-PAO lubricant.

Another object of the present invention is to provide an improved process for controlling process reaction conditions to product variable HVI-PAO product viscosities.

Yet another object of the instant invention is to provide a process for selectively varying the viscosities of HVI-PAO oligomers under essentially constant temperature oligomerization reaction conditions.

SUMMARY OF THE INVENTION

An improved process has been discovered to produce liquid #oligomers from alpha-olefins feedstock, such as 1-decene, wherein said oligomers have branch ratios below 0.19 and have higher viscosity indices than oligomers with higher branch ratios. The olefins can be oligomerized over a supported and reduced metal oxide catalyst from Group VIB of the Periodic Table to give oligomers suitable for lubricant application. Suprisingly, it has been found that in the oligomerization of the olefins in a fixed bed reactor containing extruded catalyst the viscosity of the lubricant produced can be selectively controlled by varying the olefin feedstock weight hourly space velocity (WHSV), based on catalyst, at essentially constant oligomerization temperature.

More particularly, in a process for the preparation of liquid hydrocarbons suitable as lubricant basestocks from alpha-olefin feedstock containing 6 to 20 carbon atoms, or mixtures of such olefins, comprising contacting said olefins under oligomerization conditions, at reaction temperature between 50 to 250° C. to vary product viscosity, and with a chromium catalyst on a porous support, which catalyst has been treated by oxidation at a temperature of 200° C. to 900° C. in the presence of an oxidizing gas and then by treatment with a reducing agent at a temperature and for a time sufficient to reduce said catalyst to a lower valence state to obtain an oligomeric liquid lubricant composition comprising $C_3$–$C_{1300}$ hydrocarbons, said composition having a branch ratio of less than 0.19, weight average molecular weight between 420 and 45,000, number average molecular weight between 420 and 18,000, molecular weight distribution between 1 and 5 and pour point below −15° C., the improvement comprising; oligomerizing said olefins in a fixed bed reactor in contact with extruded reduced chromium oxide catalyst on a porous support at essentially constant oligomerization temperature and varying said olefin feestock WHSV whereby lubricant product viscosity can be

DETAILED DESCRIPTION OF THE INVENTION

Figure 1:
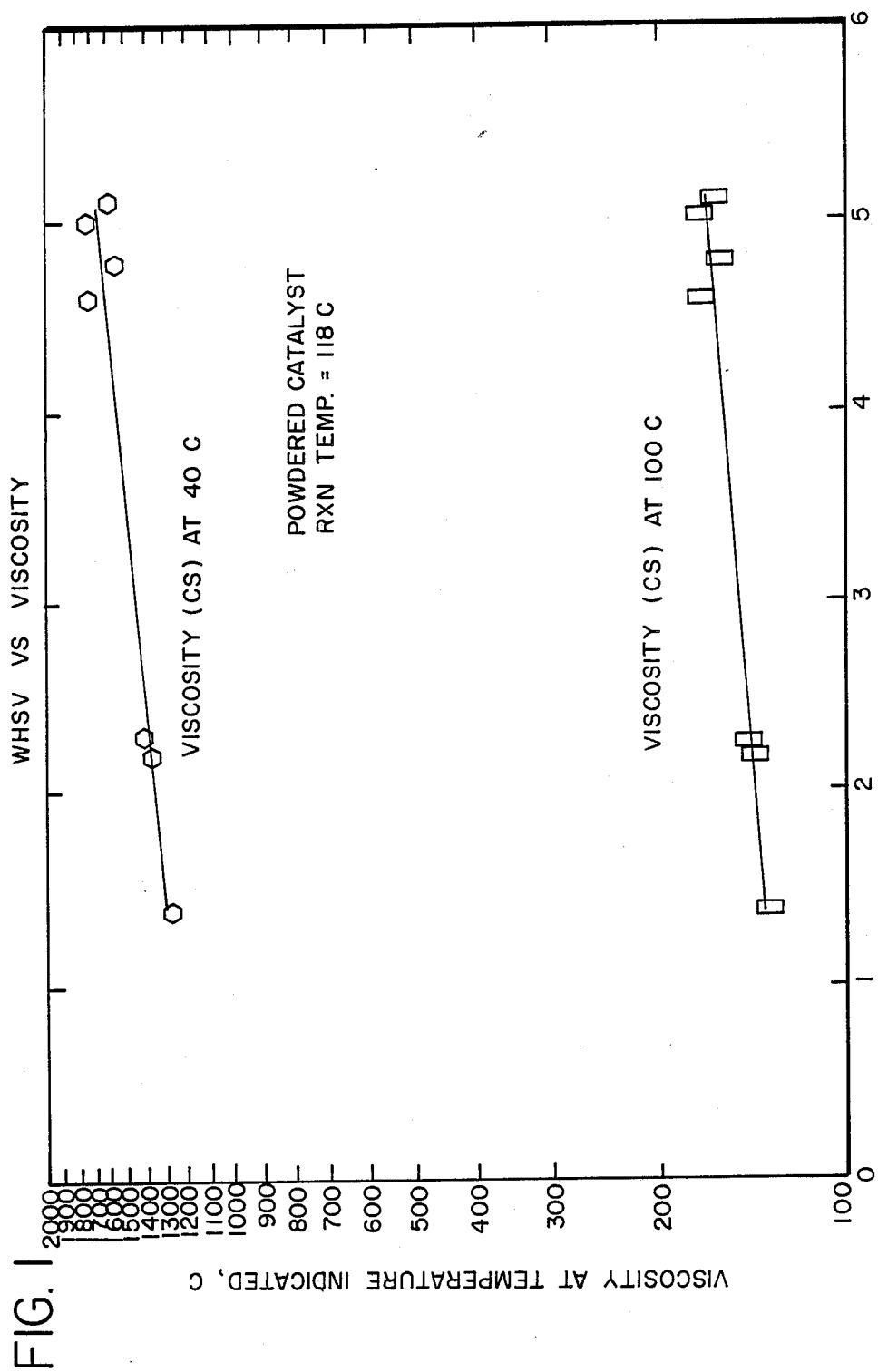
FIG. 1 is a plot of WHSV vs Viscosity for HVI-PAO of the instant invention using powdered catalyst.

In the following description, unless otherwise stated, all references to HVI-PAO oligomers or lubricants refer to hydrogenated oligomers and lubricants in keeping with the practice well known to those skilled in the art of lubricant production. As oligomerized, HVI-PAO oligomers are mixtures of dialkyl vinylidenic and 1,2-dialkyl or trialkyl mono-olefins. Lower molecular weight unsaturated oligomers are preferably hydrogenated to produce thermally and oxidatively stable, useful lubricants. Higher molecular weight unsaturated HVI/PAO oligomers are sufficiently thermally stable to be utilized without hydrogenation and, optionally, may be so employed. Both unsaturated and hydrogenated HVI-PAO of lower or higher molecular exhibit viscosity indices of at least 130 and pour point below 15° C.

The prior art process described herein to produce the novel HVI-PAO oligomers can be controlled by varying oligomerization temperature to yield oligomers having weight average molecular weight between 300 and 45,000 and number average molecular weight between 300 and 18,000. Measured in carbon numbers, molecular weights range from $C_{30}$ to $C_{1300}$ and viscosity up to 750cs at 100° C., with a preferred range of $C_{30}$ to $C_{1000}$ and a viscosity of up to 1000cs at 100° C. Molecular weight distributions (MWD), defined as the ratio of weight average molecular to number average molecular weight, range from 1.00 to 5, with a preferred range of 1.01 to 3 and a more preferred MWD of about 1.05 to 2.5. Compared to conventional PAO derived from $BF_3$ or $AlCl_3$ catalyzed polymerization of 1-alkene, HVI-PAO has been found to have a higher proportion of higher molecular weight polymer molecules in the product.

Viscosities of the novel HVI-PAO oligomers measured at 100° C. range from 3 cs to 5000 cs. The viscosity index for the new polyalpha-olefins is approximately described by the following equation:

$VI = 156.8 + 4.94 \times (V_{100}C)^{0.5}$, where $V_{100}$° C. is kinematic viscosity in centistokes measured at 100° C.

Olefins suitable for use as starting material in the preparation of HVI/PAO include those olefins containing from 2 to about 20 carbon atoms such as ethylene, propylene, 1-butene, 1-pentene, 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used in this invention are preferably alpha olefinic as for example 1-heptene to 1-hexadecene and more preferably 1-octene to 1-tetradecene, or mixtures of such olefins.

Oligomers of alpha-olefins in accordance with the invention have a low branch ratio of less than 0.19 and superior lubricating properties compared to the alpha-olefin oligomers with a high branch ratio, as produced in all known commercial methods.

This new class of alpha-olefin oligomers are prepared by oligomerization reactions in which a major proportion of the double bonds of the alpha-olefins are not isomerized. These reactions include alpha-olefin oligomerization by supported metal oxide catalysts, such as Cr compounds on silica or other supported IUPAC Periodic Table Group VIB compounds. The catalyst most preferred is a lower valence Group VIB metal oxide on an inert support. Preferred supports include silica, alumina, titania, silica alumina, magnesia and the like. The support material binds the metal oxide catalyst. Those porous substrates having a pore opening of at least 40 angstoms are preferred.

The support material usually has high surface area and large pore volumes with average pore size of 40 to about 350 angstroms. The high surface area are beneficial for supporting a large amount of highly despersive, active chromium metal centers and to give maximum efficiency of metal usage, resulting in very high activity catalyst. The support should have large average pore openings of at least 40 angstroms, with an average pore opening of 60 to 300 angstroms preferred. This large pore opening will not impose any diffusional restriction of the reactant and product to and away from the active catalytic metal centers, thus further optimizing the catalyst productivity. Also, for this catalyst to be used in fixed bed or slurry reactor and to be recycled and regenerated many times, a silica support with good physical strength is preferred to prevent catalyst particle attrition or disintegration during handling or reaction.

The supported metal oxide catalysts are preferably prepared by impregnating metal salts in water or organic solvents onto the support. Any suitable organic solvent known to the art may be used, for example, ethanol, methanol, or acetic acid. The solid catalyst precursor is then dried and calcined at 200° to 900° C. by air or other oxygen-containing gas. Thereafter the catalyst is reduced by any of several various and well known reducing agents such as, for example, CO, $H_2$, $NH_3$, $H_2S$, $CS_2$, $CH_3SCH_3$, $CH_3SSCH_3$, metal alkyl containing compounds such as $R_3Al$, $R_3B$, $R_2Mg$, RLi, $R_2Zn$, where R is alkyl, alkoxy, aryl and the like. Preferred are CO or $H_2$ or metal alkyl containing compounds. Alternatively, the group VIB metal may be applied to the substrate in reduced form, such as CrII compounds. The resultant catalyst is very active for oligomerizing olefins at a temperature range from 90° C. to about 250° C. at a pressure of 0.1 atmosphere to 5000 psi. Contact time of both the olefin and the catalyst can vary from one second to 24 hours. The catalyst can be used in a batch type reactor or in a fixed bed, continuous-flow reactor.

In general the support material may be added to a solution of the metal compounds, e.g., acetates or nitrates, etc., and the mixture is then mixed and dried at room temperature. The dry solid gel is purged at successively higher temperatures to about 600° for a period of about 16 to 20 hours. Thereafter the catalyst is cooled down under an inert atmosphere to a temperature of about 250° to 450° and a stream of pure reducing agent is contacted therewith for a period when enough CO has passed through to reduce the catalyst as indicated by a distinct color change from bright orange to pale blue. Typically, the catalyst is treated with an amount of CO equivalent to a two-fold stoichiometric excess to reduce the catalyst to a lower valence CrII state. Finally the catalyst is cooled down to room temperature and is ready for use.

The product oligomers have a very wide range of viscosities with high viscosity indices suitable for high performance lubrication use. The product oligomers also have atactic molecular structure of mostly uniform heat-to-tail connections with some head-to-head type connections in the structure. These low branch ratio oligomers have high viscosity indices at least about 15 to 20 units and typically 30–40 units higher than equivalent viscosity prior art oligomers, which regularly have higher branch ratios and correspondingly lower viscosity indices. These low branch oligomers maintain better or comparable pour points.

The branch ratios defined as the ratios of $CH_3$ groups to $CH_2$ groups in the lube oil are calculated from the weight fractions of methyl groups obtained by infrared methods, published in *Analytical Chemistry*, Vol. 25, No. 10, p. 1466 (1953).

$$\text{Branch ratio} = \frac{\text{wt fraction of methyl group}}{1 - (\text{wt fraction of methyl group})}$$

The following examples of the preparation of HVI-PAO oligomers are presented merely for illustration purposes and are not intended to limit the scope of the present invention.

EXAMPLE 1

Catalyst Preparation and Activation Procedure 1.9 grams of chromium (II) acetate $(Cr_2(OCOCH_3)_4 2H_2O)$ (5.58 mmole) (commercially obtained) is dissolved in 50 cc of hot acetic acid. Then 50 grams of a silica gel of 8–12 mesh size, a surface area of 300 m²/g, and a pore volume of 1 cc/g, also is added. Most of the solution is absorbed by the silica gel. The final mixture is mixed for half an hour on a rotovap at room temperature and dried in an open-dish at room temperature. First, the dry solid (20 g) is purged with $N_2$ at 250° C. in a tube furnace. The furnace temperature is then raised to 400° C. for 2 hours. The temperature is then set at 600° C. with dry air purging for 16 hours. At this time the catalyst is cooled down under $N_2$ to a temperature of 300° C. Then a stream of pure CO (oo.99% from Matheson) is introduced for one hour. Finally, the catalyst is cooled down to room temperature under $N_2$ and ready for use.

EXAMPLE 2

The powdered catalyst prepared in Example 1 (3.2 g) is packed in a ⅜" stainless steel tubular reactor inside an $N_2$ blanketed dry box. The reactor under $N_2$ atmosphere is then heated to 150° C. by a single-zone Lindberg furnace. Pre-purified 1-hexene is pumped into the reactor at 140 psi and 20 cc/hr. The liquid effluent is collected and stripped of the unreacted starting material and the low boiling material at 0.05 mm Hg. The residual clear, colorless liquid has viscosities and VI's suitable as a lubricant base stock.

| Sample | Prerun | 1 | 2 | 3 |
|---|---|---|---|---|
| T.O.S., hr. | 2 | 3.5 | 5.5 | 21.5 |
| Lube Yield, wt. % | 10 | 41 | 74 | 31 |
| Viscosity, cS, at | | | | |
| 40° C. | 208.5 | 123.3 | 104.4 | 166.2 |
| 100° C. | 26.1 | 17.1 | 14.5 | 20.4 |
| VI | 159 | 151 | 142 | 143 |

The experiments conducted under the above condition of essentially constant temperature and WHSV produce HVI-PAO with about the safe viscosity.

EXAMPLE 3

Similar to Example 2, a fresh catalyst sample is charged into the reactor and 1-hexene is pumped to the reactor at 1 atm and 10 cc per hour. As shown below, a lube of high viscosities and high VI's is obtained. These runs show that at different reaction conditions, a lube product of high viscosities can be obtained and that viscosity can be varied with change in reaction temperature.

| Sample | A | B |
|---|---|---|
| T.O.S., hrs. | 20 | 44 |
| Temp., °C. | 100 | 50 |
| Lube Yield, cS at | | |
| 40° | 13170 | 19011 |
| 100° | 620 | 1048 |
| VI | 217 | 263 |

EXAMPLE 4

A commercial chrome/silica catalyst which contains 1% Cr on a large-pore volume synthetic silica gel is used. The catalyst is first calcined with air at 800° C. for 16 hours and reduced with CO at 300° C. for 1.5 hours. Then 3.5 g of the catalyst is packed into a tubular reactor and heated to 100° C. under the $N_2$ atmosphere. 1-Hexene is pumped through at 28 cc per hour at 1 atmosphere. The products are collected and analyzed as follows:

| Sample | C | D | E | F |
|---|---|---|---|---|
| T.O.S., hr. | 3.5 | 4.5 | 6.5 | 22.5 |
| Lube Yield, wt % | 73 | 64 | 59 | 21 |
| Viscosity, cS, at | | | | |
| 40° C. | 2548 | 2429 | 3315 | 9031 |
| 100° C. | 102 | 151 | 197 | 437 |
| VI | 108 | 164 | 174 | 199 |

These runs show that different Cr on a silica catalyst are also effective for oligomerizing olefins to lube products.

EXAMPLE 5

As in Example 4, purified 1decene is pumped through the reactor at 250 to 320 psi. The product is collected periodically and stripped of light products boiling points below 650° F. High quality lubes with high VI are obtained (see following table). The table also shows that at about the safe WHSV, the viscosity of the product decreases with

| Reaction Temp. °C. | WHSV g/g/hr | Lube Product Properties | | |
|---|---|---|---|---|
| | | V at 40° C. | V at 100° C. | VI |
| 120 | 2.5 | 1555.4 cs | 157.6 cs | 217 |
| 135 | 0.6 | 389.4 | 53.0 | 202 |
| 150 | 1.2 | 266.8 | 36.2 | 183 |
| 166 | 0.6 | 67.7 | 11.3 | 181 |
| 197 | 0.5 | 21.6 | 5.1 | 172 |

In the instant invention it has been found that by using a novel extruded or powdered catalyst which is comprised of an appropriate chromium compound impregnated on a silica matrix, activated and used in a fixed bed reactor, high viscosity index synthetic lubricants can be produced. The chemical composition of the catalyst and the support material can be taken from those compositions described above for the oligomerization of alpha-olefins to HVI-PAO oligomers. In the instant invention the catalyst can contain between 0.1 and 10 percent chromium, a pore diameter between 40 and 350 angstroms and a bulk density between 0.25 and 2 gm/cc. Preferably, the catalyst contains about 1% chromium, a pore diameter of about 200 angstroms and a bulk density of about 0.42 gm/cc. Further, in the instant invention it has been found that with extruded or powdered catalyst in a fixed bed reactor, varying alpha-olefin, or 1-alkene, feedstock weight hourly space velocity (WHSV) between 0.1 and 10, based on catalyst, can vary the viscosity of the product, at essentially constant reaction temperature. It has been found that increasing feedstock WHSV at otherwise constant conditions, surprisingly increases product viscosity. Preferably, the alpha-olefin WHSV in the instant invention is between 0.5 and 6, based on catalyst.

The following example illustrates the catalyst preparation, activation and feedstock pretreatment procedure used in the instant invention.

EXAMPLE 6

A. Catalyst Preparation 33 grams of 1/16 inch (1.59 mm) silica extrudates is placed into a 200 ml beaker. A solution of 1.52 grams of chromium acetate in 80 ml of water is added to the extrudates and allowed to stand overnight at room temperature. The excess water is removed by heating until the extrudates are damp. The damp extrudates are then placed into a rotovap at 80 ° C., under vacuum, and taken to dryness. Additional drying is made by vacuum drying at 120° C. Then resulting catalyst is described as follows:

| Catalyst Diameter, mm | 1.59 |
|---|---|
| Catalyst Length, mm | 6.35 |
| Surface Area, sq. M/Gm | 200 |
| Pore Diameter, Angstroms | 200 |
| Chromium Loading wt. % | 1.09 |
| Bulk Density, Gm/cc | 0.42 |

B. Catalyst Activation 10 grams (23 ml) of the above catalyst is placed into a stainless steel, fixed bed reactor whose inside diameter is ⅝ inches (15.9 mm). The length of the catalyst bed is six inches. The interstitial spaces between the extrudates is packed with 70/80 mesh sand. The chromium on silica extrudate catalyst is activated by predrying with dry nitrogen at 260° C., overnight. The caalyst bed is then calcined in air, at 200cc/min, from 250° to 600° C., at 1° C./minute and held at 600° C. for 12 hours. At the end of 12 hours, the temperature is reduced to 350° C. At this temperature, carbon monoxide, at 200 cc/min, is contacted with the catalyst for 30 minutes to reduce the chromium.

C. Pretreatment of 1-alkene

Prior to contacting the catalyst with the feed, the 1-alkene, such as 1decene, is treated to remove catalyst poisons. The treatment consists of passing the feed over activated molecular sieves to remove traces of water and polar compounds such as decanol. The feed is further contacted with a reduced copper/chromia catalyst to remove peroxides. A final contact with predried 5A sieves is made. The feed pretreatment is made on a continuous basis before the feed enters the fixed bed reactor.

In Table 1, the results of the oligomerization of 1-decene using the catalyst of Example 6 is described as well as the oligomerization conditions.

TABLE 1

| | 1 | 2 | 3 |
|---|---|---|---|
| Temperature, °C. | 123 | 150 | 182 |
| Pressure, psig | 100 | 100 | 100 |
| WHSV | 0.45 | 2.33 | 2.32 |
| Grams Feed | 232 | 477 | 468 |
| Grams Product | 188 | 351 | 298 |
| % Yield | 81.2 | 73.6 | 63.3 |
| Viscosity, cS, 40° C. | 755.3 | 379.5 | 86.2 |
| Viscosity, cS, 100° C. | 88.1 | 46.4 | 13.6 |
| Viscosity Index | 206 | 182 | 161 |

The above table shows the effect of reactor temperature on the final product viscosity. As reactor temperature is raised a corresponding decrease in product viscosity is noted.

In the following Examples 7 and 8 the discovery of the instant invention is illustrated using powdered catalyst (Example 7) and extruded catalyst (Example 8) prepared as described in Example 6.

EXAMPLE 7

While maintaining a reactor temperature of 118° C., 1decene is fed to the catalyst bed of powdered catalyst wherein it undergoes oligomerization to produce a synthetic lubricant HVI-PAO. The WHSV is varied from 1.4 to 5.0 and product is collected after an appropriate line-out period. Viscosity measurements, using conventional equipment, are made at 40° C. and 100° C. In Table 2 are shown the results of the viscosity measurements at different WHSV's using the powdered catalyst. It is clear that as the WHSV is raised, the viscosity of the resulting lubricant increases. This relationship, at the two measurement temperatures, is also shown in FIG. 1. For the conditions used, the maximum increase in viscosity is about 29% for the viscosity measured at

TABLE 2

Powdered Catalyst
Product Viscosity Vs Feedstock WHSV

| WHSV | KV, 40° C. | KV, 100° C. |
|---|---|---|
| 1.4 | 1258 | 134 |
| 2.2 | 1355 | 142 |
| 2.3 | 1389 | 144 |
| 4.6 | 1710 | 169 |
| 4.8 | 1532 | 157 |
| 5.0 | 1695 | 170 |

TABLE 2-continued

| Powdered Catalyst Product Viscosity Vs Feedstock WHSV | | |
|---|---|---|
| WHSV | KV, 40° C. | KV, 100° C. |
| 5.1 | 1564 | 161 |

EXAMPLE 8

Figure 2:
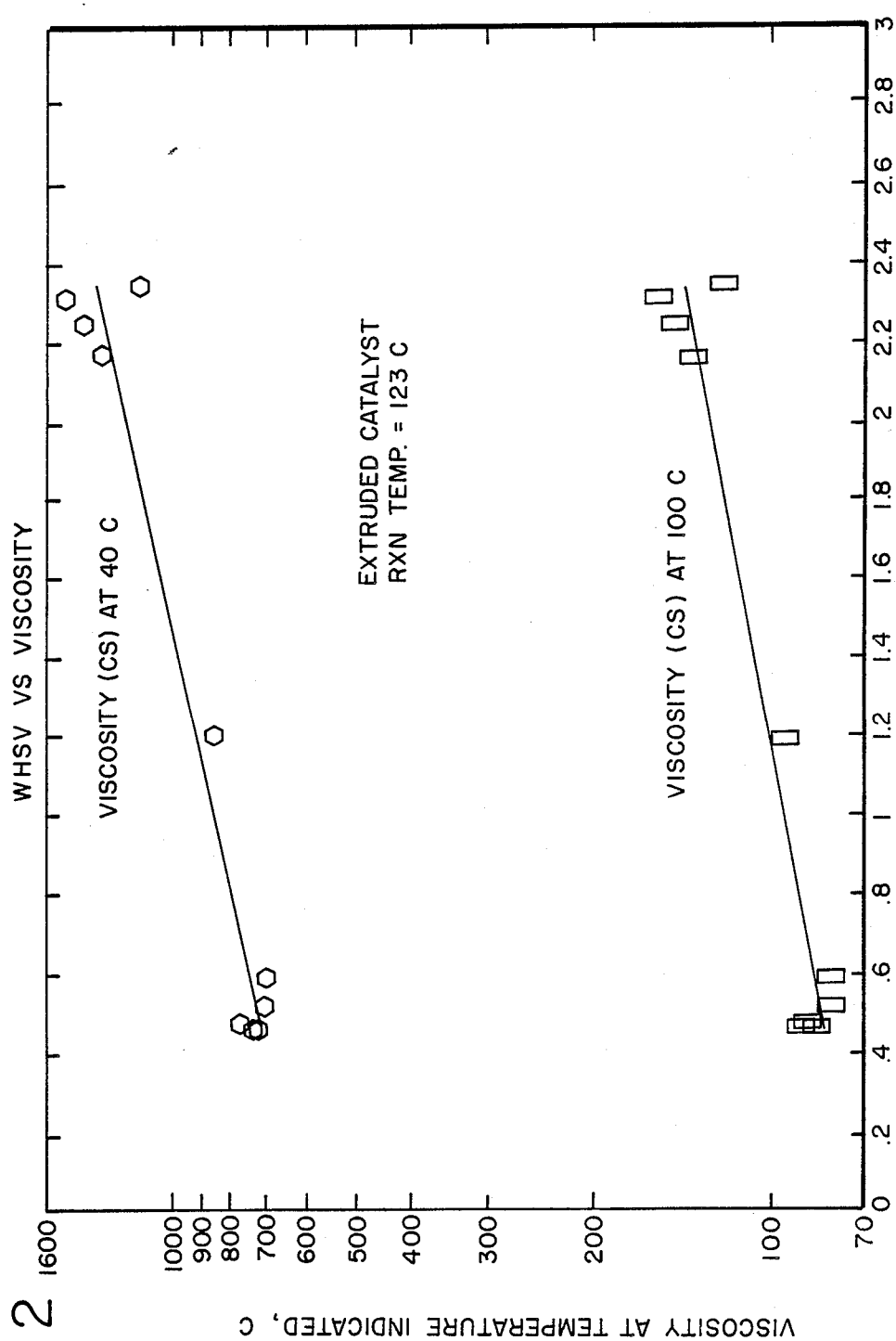
FIG. 2 is a plot of WHSV vs Viscosity for HVI-PAO of the instant invention using extruded catalyst.

A similar oligomerization of 1-decene is made using an extruded version of the reduced chromium on silica catlyst described in Example 6. The reaction temperature is 123° C. The same conclusion can be drawn as with the powdered catalyst. As the feedstock WHSV is increased, the product viscosity also increases. These results are shown in Table 3 and FIG. 2. In this case, the increase in viscosity is 82% when measured at 40° C.

Figure 3:
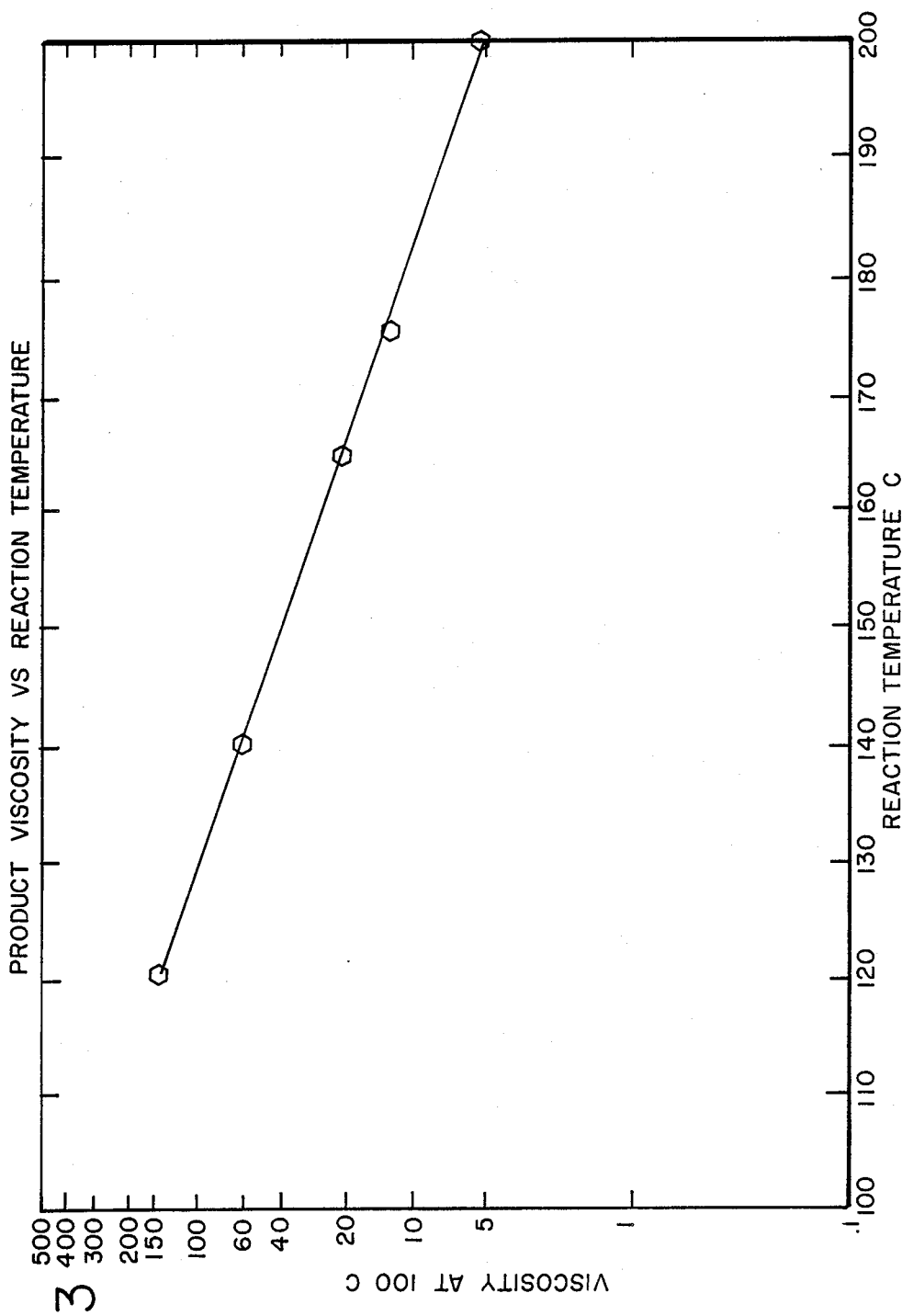
FIG. 3 is a plot of HVI-PAO product viscosity vs reaction temperature.

For comparison the change is viscosity with reaction temperature is shown in FIG. 3. This is the only other means of altering product viscosity.

TABLE 3

| Extruded Catalyst Product Viscosity Vs Feedstock WHSV | | |
|---|---|---|
| WHSV | KV, 40° C. | KV, 100° C. |
| 0.5 | 734 | 91 |
| 0.5 | 719 | 85 |
| 0.5 | 697 | 80 |
| 0.5 | 767 | 89 |
| 0.6 | 700 | 80 |
| 1.2 | 849 | 95 |
| 2.2 | 1293 | 134 |
| 2.3 | 1398 | 144 |
| 2.3 | 1470 | 151 |
| 2.4 | 1134 | 120 |

Although the present invention has been described with preferred embodiments and examples, modifications and variations may be resorted to without departing from the spirit and scope of this understanding. Such modifications and variations are considered to be within the purview and scope of the appended claims.

What is claimed is:

1. In a process for the preparation of liquid hydrocarbons suitable as lubricant basestocks from alpha-olefin feedstock containing 6 to 20 carbon atoms, or mixtures of such olefins, comprising contacting said olefins under oligomerization conditions, at reaction temperature between 90° to 250° C. to vary product viscosity, and with a chromium catalyst on a porous support, which catalyst has been treated by oxidation at a temperature of 200° C. to 900° C. in the presence of an oxidizing gas and then by treatment with a reducing agent at a temperature and for a time sufficient to reduce said catalyst to a lower valence state to obtain an oligomeric liquid lubricant composition comprising $C_{30}$–$C_{1300}$ hydrocarbons, said composition having a branch ratio of less than 0.19, weight average molecular weight between 420 and 18,000, molecular weight distribution between 1 and 5 and pour point below −15° C., the improvement comprising; oligomerizing said olefins in a fixed bed reactor in contact with extruded reduced chromium oxide catalyst on a porous support at essentially constant oligomerization temperature and varying said olefin feedstock WHSV based on catalyst whereby said liquid lubricant hydrocarbon product viscosity can be selectively varied.

2. The process according to claim 1 wherein said improvement comprises increasing said feedstock WHSV at essentially constant oligomerization temperature whereby lubricant product viscosity is increased.

3. The process of claim 1 wherein said extruded catalyst contains between 0.1 and 10 percent chromium; said catalyst having pore diameter between 40 and 350 angstroms and bulk density between 0.25 and 2 gm/cc.

4. The process of claim 2 wherein said catalyst contains about 1% chromium; pore diameter of about 200 angstroms; and bulk density of about 0.42 gm/cc.

5. The process of claim 1 wherein said improvement comprises oligomerizing said olefin in contact with powdered catalyst.

6. The process of claim 1 wherein said feedstock WHSV at essentially constant temperature is between 0.1 and 10, based on catalyst.

7. The process of claim 1 wherein said feedstock WHSV at essentially constant temperature is between 0.5 and 6, based on catalyst.

8. The process of claim 1 wherein said liquid lubricant hydrocarbon product has a viscosity index greater than 130.

9. The process of claim 1 wherein said porous support comprises silica and said catalyst is reduced with carbon monoxide.

10. A process for the production of liquid hydrocarbon basestock comprising; contacting $C_6$–$C_{20}$ 1-alkene feedstock in a fixed bed with reduced valence state extruded Group VIB metal catalyst on porous support in an oligomerization zone under oligomerization conditions at constant temperature and varying 1-alkene feedstock weight average space velocity (WHSV based on catalyst whereby said basestock is produced at viscosity varying in correspondence with said WHSV said basestock having a branch ratio less than 0.19 and pour point below −15° C.

11. The process of claim 10 wherein said metal catalyst comprises CO reduced chromium oxide; said porous support comprises silica; said feedstock comprises 1-decene and said basestock has a viscosity index greater than 130.

* * * * *

UNITED STATES PATENT AND TRADEMARK OFFICE
CERTIFICATE OF CORRECTION

PATENT NO. : 4,914,254
DATED : April 3, 1990
INVENTOR(S) : Bruce P. Pelrine

It is certified that error appears in the above-identified patent and that said Letters Patent is hereby corrected as shown below:

Column 3, line 9; after "can be" insert --selectively varied.--

Column 5, line 15; "heat-to-tail" should be --head-to-tail--

Column 6, line 62; "1 decene" should be --1-decene--

Column 6, line 68; after "with" insert --increasing reaction temperature (135,166, 197°C).--

Column 7, line 68; "caalyst" should be --catalyst--

Column 8, line 10; "1decene" should be --1-decene--

Column 8, line 45; "1decene" should be --1-decene--

Column 8, line 57; after "at" insert --40°C.--

Column 9, line 12; "catlyst" should be --catalyst--

UNITED STATES PATENT AND TRADEMARK OFFICE
CERTIFICATE OF CORRECTION

PATENT NO. : 4,914,254

DATED : April 3, 1990

INVENTOR(S) : Bruce P. Pelrine

It is certified that error appears in the above-identified patent and that said Letters Patent is hereby corrected as shown below:

Column 10, line 44; "(WHSV" should be --(WHSV)--

Signed and Sealed this

Tenth Day of September, 1991

*Attest:*

HARRY F. MANBECK, JR.

*Attesting Officer*     *Commissioner of Patents and Trademarks*